US012708790B2

(12) United States Patent
Feliciano et al.

(10) Patent No.: US 12,708,790 B2
(45) Date of Patent: Aug. 18, 2026

(54) APPLICATOR WITH RADIATING ELEMENTS

(71) Applicant: L'Oreal, Paris (FR)

(72) Inventors: Rafael Feliciano, New Providence, NJ (US); Gregoire Charraud, Jersey City, NJ (US)

(73) Assignee: L'Oreal, Paris (FR)

( * ) Notice: Subject to any disclaimer, the term of this patent is extended or adjusted under 35 U.S.C. 154(b) by 300 days.

(21) Appl. No.: 18/345,194

(22) Filed: Jun. 30, 2023

(65) Prior Publication Data

US 2025/0001198 A1 Jan. 2, 2025

(51) Int. Cl.
*A61N 5/06* (2006.01)
*A45D 34/04* (2006.01)
*A61F 7/00* (2006.01)

(52) U.S. Cl.
CPC ......... *A61N 5/0616* (2013.01); *A45D 34/041* (2013.01); *A45D 2200/205* (2013.01)

(58) Field of Classification Search
CPC ................ A61N 5/0616; A45D 34/041; A45D 2200/205; A61F 2007/0001–005
See application file for complete search history.

(56) References Cited

U.S. PATENT DOCUMENTS

| | | | | |
|---|---|---|---|---|
| 11,278,351 | B2 * | 3/2022 | Dresser .................. | A61B 18/22 |
| 2006/0103905 | A1 * | 5/2006 | Walmsley .......... | G02B 19/0014 359/198.1 |
| 2010/0049177 | A1 * | 2/2010 | Boone, III ........... | A61H 9/0057 606/9 |
| 2010/0210993 | A1 | 8/2010 | Flyash et al. | |
| 2012/0209151 | A1 * | 8/2012 | Zhou .................... | A61N 5/0616 601/2 |
| 2013/0282085 | A1 | 10/2013 | Lischinsky et al. | |
| 2016/0045762 | A1 * | 2/2016 | Gurovich ............. | A61B 18/203 607/88 |
| 2016/0058156 | A1 * | 3/2016 | Chiasson ............. | A45D 40/261 132/200 |
| 2018/0168318 | A1 * | 6/2018 | Streeter .................. | A45D 33/32 |
| 2020/0038530 | A1 * | 2/2020 | Yildirim ................... | A61L 2/14 |
| 2020/0298016 | A1 * | 9/2020 | Yoon .................... | A61N 5/0616 |
| 2021/0268299 | A1 | 9/2021 | Casalino et al. | |
| 2022/0032083 | A1 * | 2/2022 | Austen ................. | A61N 5/0617 |

FOREIGN PATENT DOCUMENTS

KR 20200050488 A 5/2020

OTHER PUBLICATIONS

Preliminary Search Report and Written Opinion mailed Mar. 8, 2024, issued in corresponding French Application No. 2309706, filed Sep. 14, 2023, 6 pages.

* cited by examiner

*Primary Examiner* — Adam Z Minchella
(74) *Attorney, Agent, or Firm* — Christensen O'Connor Johnson Kindness PLLC

(57) ABSTRACT

An applicator including an applicator surface configured to apply one or more formulas, one or more reservoirs configured to hold the one or more formulas, a condition sensor configured to detect one or more conditions as the applicator surface moves across skin, and one or more radiating elements, where the one or more radiating elements are configured to emit one or more radiation treatments into the skin.

19 Claims, 10 Drawing Sheets

APPLICATOR WITH RADIATING ELEMENTS

SUMMARY

In one aspect, disclosed herein is an applicator including an applicator surface configured to apply one or more formulas, one or more reservoirs configured to hold the one or more formulas, a condition sensor configured to detect one or more conditions as the applicator surface moves across skin, and one or more radiating elements, where the one or more are configured to emit one or more radiation treatments into the skin.

In some embodiments, the one or more radiating elements comprise one or more antennas. In some embodiments, the applicator is configured to apply the one or more radiation treatments to one or more treatment areas.

In some embodiments, one or more radiation treatments include emitting one or more beams of radiation from the one or more radiating elements. In some embodiments, the one or more beams of radiation include emitting a central beam of radiation, where the central beam extends to a first depth. In some embodiments, the one or more radiation treatments include directing the central beam towards the one or more conditions.

In some embodiments, the one or more radiation treatments further include emitting one or more lobe beams, where each lobe of the one or more lobe beams extends to a second depth. In some embodiments, the first depth is deeper than the second depth. In some embodiments, the second depth is deeper than the first depth. In some embodiments, the one or more radiation treatments further include emitting the central beam at a first intensity substantially equally to one or more layers of the skin.

In some embodiments, the one or more radiation treatments include emitting a plurality of beams of radiation at a first intensity, and overlapping the plurality of beams of radiation, so that an overlap of the plurality of beams receives radiation energy at a second intensity. In some embodiments, the first intensity is higher than the second intensity. In some embodiments, the first intensity is lower than the second intensity.

In another aspect, disclosed herein is a system of applying a radiation treatment, the system including the applicator disclosed herein, and a dispensing device configured to couple with the applicator, the dispensing device including a processor configured to direct the dispensing device to apply the one or more radiation treatments, and direct the dispensing device to apply the one or more formulas to the skin. In some embodiments, the system further includes a communication device communicatively coupled with the dispensing device.

In yet another aspect, disclosed herein is a method of using the system as disclosed herein. In some embodiments, the method includes applying the one or more formulas to the skin, and applying the one or more radiation treatments to the skin. In some embodiments, the method further includes emitting a central beam of radiation at a first depth. In some embodiments, the method further includes emitting one or more lobes of radiation at a second depth. In some embodiments, the method further includes directing the beam to the one or more conditions.

In some embodiments, the method further includes emitting a plurality of beams of radiation at a first intensity, and overlapping the plurality of beams of radiation, so that an overlap of the plurality of beams receives radiation energy at a second intensity.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Disclosed herein are applicators, systems, and methods for applying one or more radiation treatments (or radiation therapy) to one or more layers of skin. In some embodiments, an applicator includes an applicator surface, one or more formula reservoirs, a position sensor configured to determine a position of the applicator on the skin, and a condition sensor configured to determine one or more conditions of the skin. In some embodiments, the position and/or the condition determines an amount of one or more formulas applied to the skin and/or a frequency, depth, power, or amplitude of the one or more radiation treatments.

In some embodiments, the one or more radiation treatments include emitting a central beam of radiation from one or more. In some embodiments, the one or more are located on or behind the applicator surface. In some embodiments, the one or more radiating elements are configured to emit a plurality of beams of radiation.

In some embodiments, the one or more radiation treatments include directing one or more beams of radiation to one or more treatment areas, and/or one or more conditions of the skin. As described herein, one or more treatment areas is understood to mean one or more areas of the skin where formula has been applied. In some embodiments, the one or more treatment areas may also be one or more conditions of the skin.

In some embodiments, the one or more radiation treatments include emitting a plurality of radiation beams at a first intensity, and overlapping the plurality of radiation beams, so that at an overlap of the plurality of radiation beams (also referred to herein as a treatment zone) receives radiation energy at a second intensity. In some embodiments, the first intensity may be higher or lower than the second intensity.

Figure 1B:
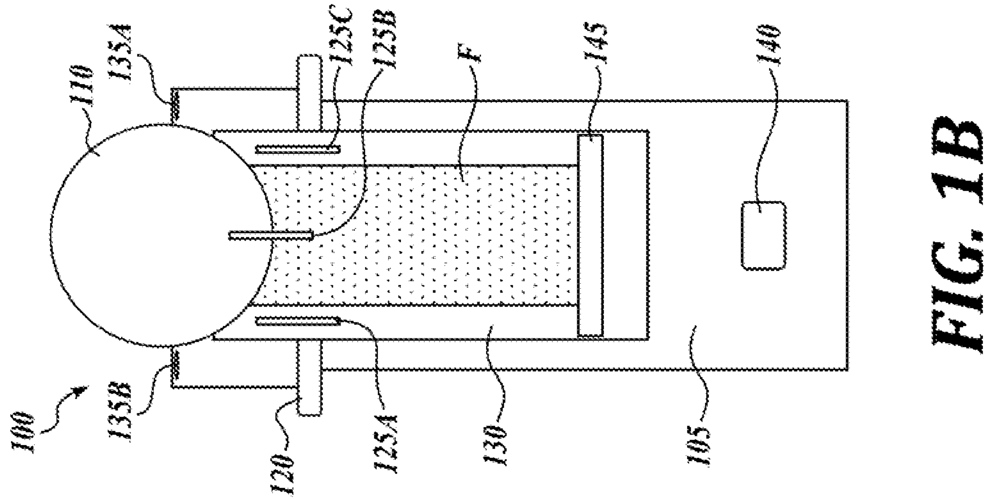
FIG. 1B is an example cross-sectional view of the applicator of FIG. 1A, in accordance with the present technology.
Figure 1A:
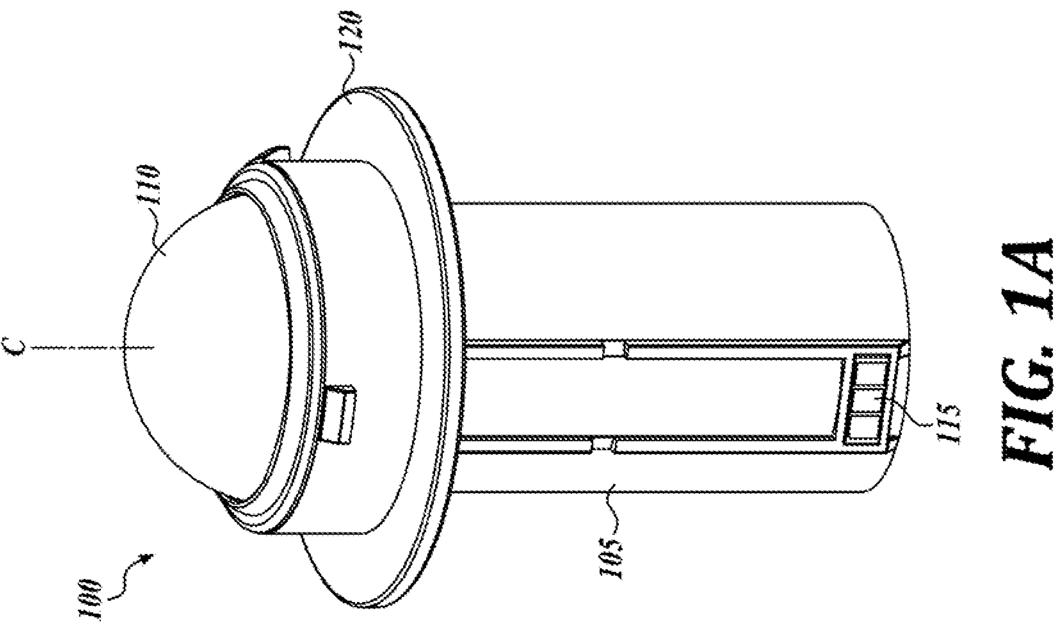
FIG. 1A is an example applicator, in accordance with the present technology.

FIG. 1A is an example applicator 100, in accordance with the present technology. The applicator 100 may include a body 105, an applicator surface 110, a tag 115, and an platform 120. Also illustrated is a cross-section line C.

In some embodiments, the applicator 100 includes a body 105. In some embodiments, the body 105 is configured to contain additional components and/or circuitry, as shown in FIG. 1B.

The applicator surface 110 may take any number of forms, including a roller ball configured to distribute and apply a formula located a reservoir inside the applicator 100 (as shown in FIGS. 1A-1B). In some embodiments, the roller ball 110 is plastic, but in other embodiments, the roller ball 110 may be glass or metal. In some embodiments, the roller ball is transparent.

Figure 4:
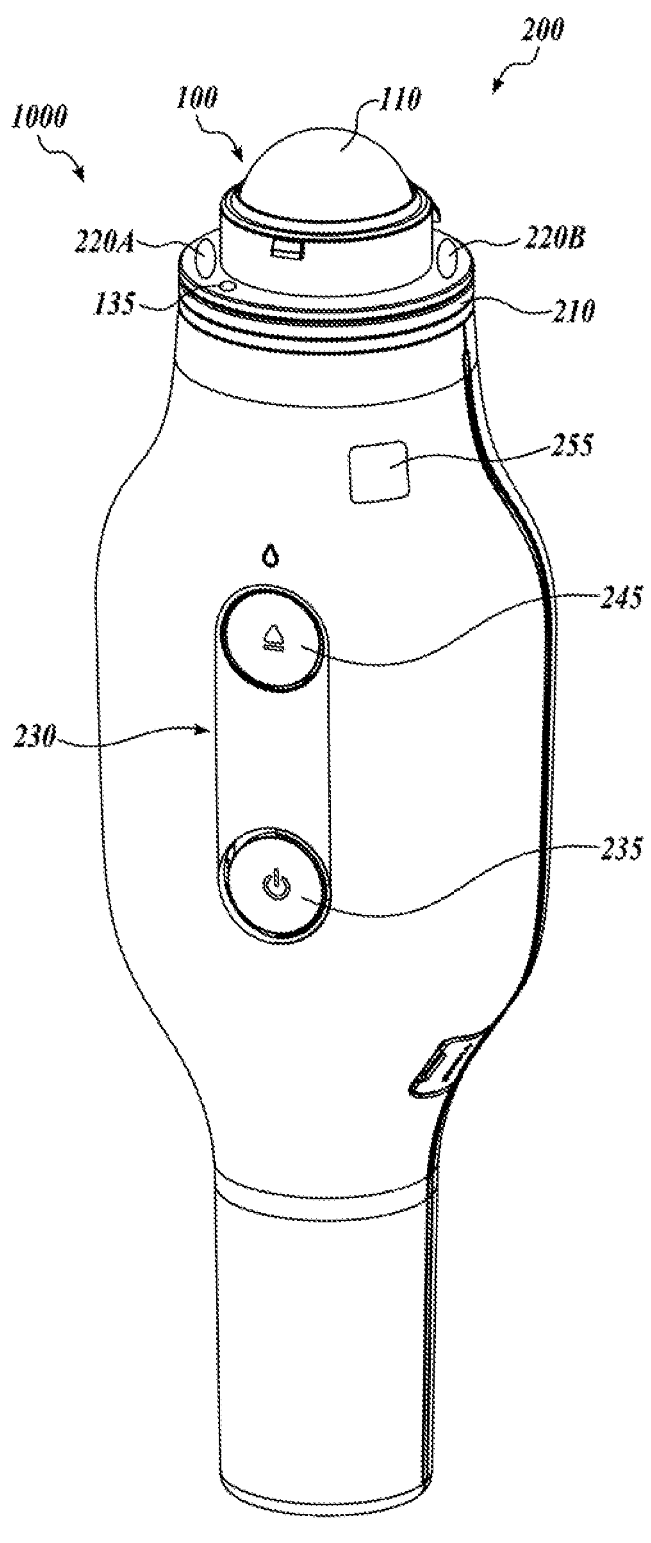
FIG. 4 is an example system, in accordance with the present technology.

In some embodiments, the applicator 100 further includes a tag 115. In some embodiments, the tag 115 is a quick response (QR) code, radiofrequency identification (RFID) tag, barcode, or the like. In some embodiments, the tag 115 communicates an identity of the applicator 100 or one or more formulations inside the applicator 100 to a dispensing device, such as shown in FIG. 4. In some embodiments, the tag 115 may be used to identify any number of things about the one or more formulas or applicator 100, including the amount of formula inside the applicator 100, the expiration date of the formula inside the applicator 100, or when to replace the applicator 100.

Figures 2A, 2B:
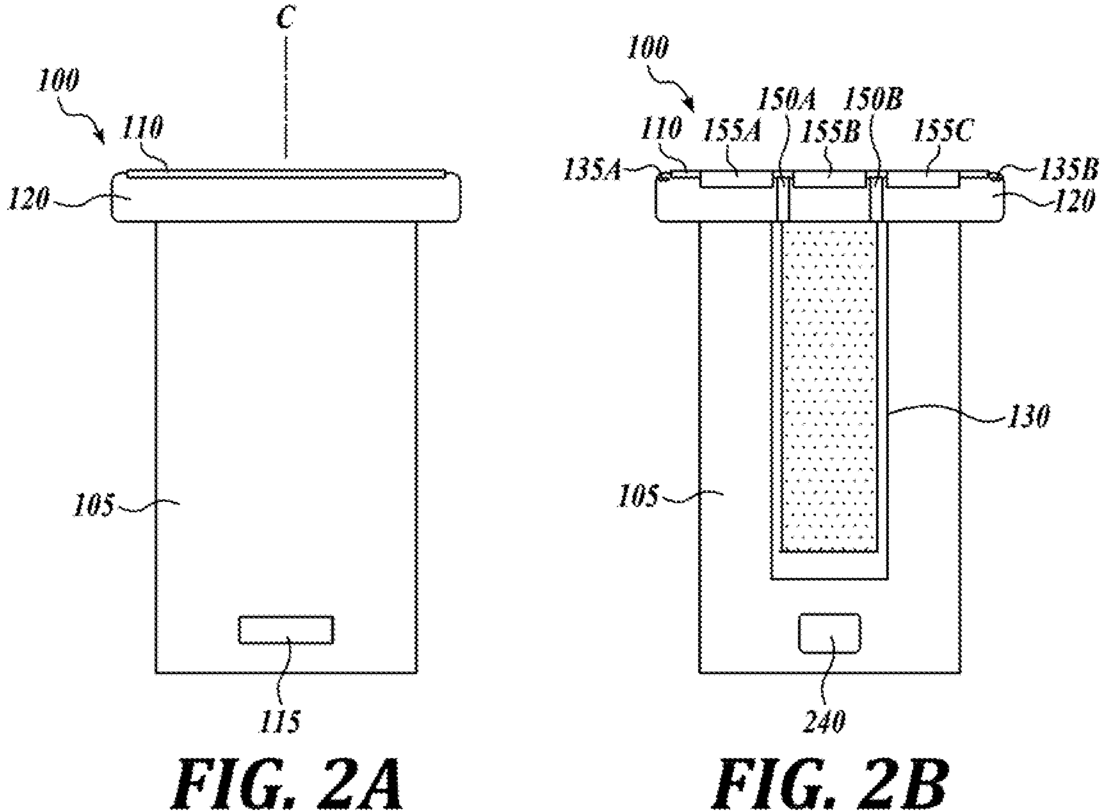
FIG. 2A is another example applicator, in accordance with the present technology.
FIG. 2B is an example cross-sectional view of the applicator of FIG. 2A, in accordance with the present technology.

In some embodiments, the applicator 100 also includes a platform 120 configured to secure the applicator 100 into a dispensing device, such as the dispensing device 200 in FIG. 4. While the platform 120 is illustrated as a disk configured to couple to a dispensing device, the platform 120 may take any form capable of securing the applicator to a dispensing device including a threaded attachment, a magnet, or an attachment configured to snap into the dispensing device. In some embodiments, the platform 120 is clear so that the dispensing device is visible through the attachment. The attachment may contain one or more sensors, as shown in FIGS. 1B, 2B, and 4.

In operation, the applicator 100 may be placed inside a dispensing device (as shown in FIG. 4) and secured to the dispensing device with the platform 120. The roller ball 110 may be rolled over a surface, such as a user's skin, to apply a formula.

FIG. 1B is an example cross-sectional view of the applicator 100 of FIG. 1A, in accordance with the present technology. FIG. 1B is a cross-section along cross-section line C in FIG. 1A. In some embodiments, the applicator 100 is configured to administer one or more radiation treatments, such as those shown in FIGS. 3A-3C. In some embodiments, the applicator 100 further includes one or more sensors 135A, 135B and one or more radiating elements 125A, 125B, 125C. While three radiating elements 125A, 125B, 125C are illustrated in FIG. 1B, it should be understood that any number of radiating elements 125A, 125B, 125C may be incorporated into applicator 100. In some embodiments, the 125A, 125B, 125C are antennas. In some embodiments, the radiating elements 125A, 125B, 125C are located behind and around the applicator surface 110 as shown in FIG. 1B. In some embodiments, the radiating elements 125A, 125B, 125C are configured to produce one or more beams of radiation energy and direct the radiation energy to the skin.

In some embodiments, the one or more sensors 135A, 135B are configured to detect a condition of a portion of the skin and determine an intensity, power, amplitude, or frequency of the radiation energy. In some embodiments, one or more sensors 135A, 135B may include a condition sensor 135A to detect a condition of the skin and determine whether to administer one or more treatments, including applying one or more formulas F from the formula reservoir 130, the radiation therapy, or combinations thereof. In some embodiments, the condition sensor 135A is a hydration sensor, a reflectance sensor, or an optical sensor, such as a camera. In some embodiments, the one or more sensors 135A, 135B may include a position sensor 135B configured to determine a position of the applicator 100 on the skin. In some embodiments, the position sensor 135B is an accelerometer, a gyroscope, or an optical sensor. In some embodiments, the one or more sensors 135A, 135B may be a single sensor configured to detect both a position of the applicator 100 and a condition of the skin.

In some embodiments, the formula reservoir 130 is located inside the body 105, and is configured to hold a formula F. In some embodiments, the formula F is a skin care formula. In some embodiments, the skin care formula is a moisturizer, a toner, an acne treatment, a wrinkle treatment, fine line treatment, or a cosmetic. As the applicator surface, illustrated here as a roller ball 110, moves or rolls, formula F from the formula reservoir 130 is applied to a surface. In some embodiments, the applicator 100 includes any number of formula reservoirs 130.

In some embodiments, the applicator 100 further includes a piston 145 configured to push the formula F towards the roller ball 110 as the formula F is applied. In some embodiments, the piston 145 is directed by circuitry on a dispensing device or on the applicator 100 itself, such as applicator processor 140 to push the formula F towards the applicator surface 110.

In some embodiments, the applicator 100 includes an applicator processor 140. In some embodiments, the applicator processor 140 is configured to direct the piston to push the formula F towards the applicator surface 110. In some embodiments, the applicator processor 140 may further be configured to detect a condition of the skin and/or a position of the applicator 100 with one or more sensors 135A, 135B as described herein, and/or to direct the applicator 100 to apply one or more treatments, as described herein.

FIG. 2A is another example applicator 100, in accordance with the present technology. In some embodiments, the applicator includes a body 105, an platform 120, an applicator surface 110, and a tag 115.

In some embodiments, the applicator includes a flat applicator surface 110. In operation, the applicator surface 110 may be moved across the skin. In some embodiments, the applicator surface 110 is the same size and length as the platform 120. In some embodiments, the applicator surface 110 is integrated into the platform 120. In some embodiments, the applicator surface includes one or more nozzles, as shown in FIG. 2B.

FIG. 2B is an example cross-sectional view of the applicator 100 of FIG. 2A, in accordance with the present technology. FIG. 2C is a cross-section along cross section line C in FIG. 2A. In some embodiments, the applicator 100 includes a reservoir 130 configured to hold a formula F, and one or more radiating elements 125A. 125B. 125C on an applicator surface 110 having one or more nozzles 150A, 150B.

In some embodiments, the applicator 100 is configured to administer one or more radiation treatments. In some embodiments, the applicator 100 further includes one or more sensors 135A, 135B and one or more radiating elements 125A, 125B, 125C. While three radiating elements 125A, 125B, 125C are illustrated in FIG. 1B, it should be understood that any number of radiating elements 125A, 125B, 125C may be incorporated into the applicator 100. In some embodiments, the 125A, 125B, 125C are antennas. In some embodiments, the radiating elements 125A, 125B, 125C are located on the applicator surface 110. In some embodiments, the radiating elements 125A, 125B, 125C are configured to produce one or more beams of radiation energy, directed towards the skin.

In some embodiments, the one or more sensors 135A, 135B are configured to detect a condition of a portion of the skin and determine an intensity, power, amplitude, or frequency of the radiation energy. In some embodiments, one or more sensors 135A, 135B may include a condition sensor 135A to detect a condition of the skin and determine whether to administer one or more treatments, including applying one or more formulas F from the formula reservoir 130, the radiation therapy, or combinations thereof. In some embodiments, the condition sensor 135A is a hydration sensor, a reflectance sensor, or an optical sensor, such as a camera. In some embodiments, the one or more sensors 135A, 135B may include a position sensor 135B configured to determine a position of the applicator 100 on the skin. In some embodiments, the position sensor 135B is an accelerometer, a gyroscope, or an optical sensor. In some embodiments, the one or more sensors 135A, 135B may be a single sensor configured to detect both a position of the applicator 100 and a condition of the skin.

In some embodiments, the one or more reservoirs 130 is located inside the body 105, and is configured to hold one or more formulas F. In some embodiments, the one or more formulas F are a skin care formula. In some embodiments, the skin care formula is a moisturizer, a toner, an acne treatment, a wrinkle treatment, fine line treatment, or a cosmetic. As the applicator surface, illustrated here as a flat applicator surface 110, moves across the surface formula F from the reservoir 130 is applied to the surface through one or more nozzles 150.

In some embodiments, the applicator 100 further includes a piston 145 configured to push the formula F towards the one or more nozzles 150A, 150B, 150C as the formula F is applied. In some embodiments, the piston 145 is directed by circuitry on a dispensing device or on the applicator 100 itself (such as applicator processor 240) to push the formula F towards the applicator surface 110.

In some embodiments, the applicator 100 includes an applicator processor 240. In some embodiments, the applicator processor 240 is configured to direct the piston to push the formula 240 towards the applicator surface 110. In some embodiments, the applicator processor 240 may further be configured to detect a condition of the skin with one or more sensors as described herein, and/or to direct the applicator 100 to apply one or more treatments, as described herein.

Figure 3A:
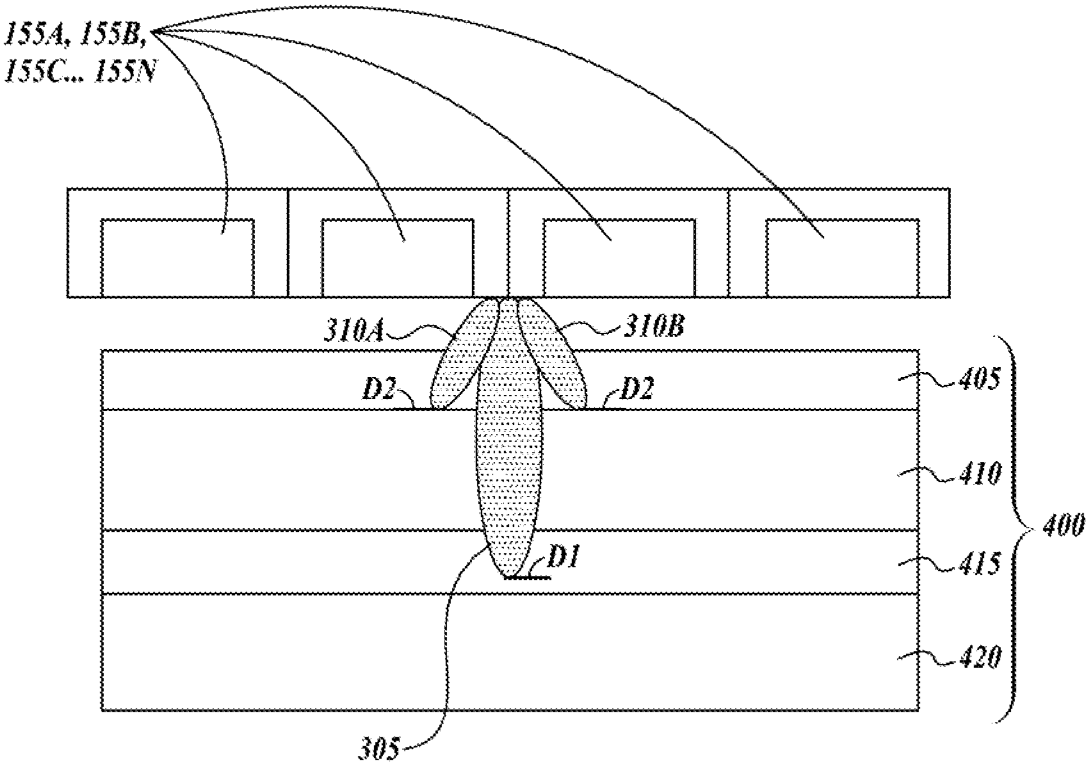
FIG. 3A is an example radiation treatment, in accordance with the present technology.

FIG. 3A is an example radiation treatment 305, 310A, 310B, in accordance with the present technology. A plurality of radiating elements 155A, 155B, 155C . . . 155N are illustrated, administering an example radiation treatment 305, 310A, 310B into one or more layers 405, 410, 415, 420, of skin 400.

In some embodiments, the radiation treatment 305, 310A, 310B is administered with one or more radiating elements 155A, 155B, 155C . . . 155N. While four radiating elements 155A, 155B, 155C . . . 155N are shown, it should be understood that there may be any number of radiating elements in the plurality of radiating elements 155A, 155B, 155C . . . 155N. It should be understood that the one or more radiating elements 155A, 155B, 155C . . . 155N may be coupled to or otherwise integrated into an applicator, such as shown in FIGS. 1A-1B and 2A-2B. The applicator and other components described have been omitted for clarity. In some embodiments, the radiating elements 155A, 155B, 155C . . . 155N may be a standalone device or separate energy capsule.

The one or more radiating elements 155A, 155B, 155C . . . 155N are configured to administer radiation therapy into one or more layers 405, 410, 415, 420 of skin 400. The skin 400 includes an epidermis layer 405, a dermis layer 410, a subcutaneous tissue layer 415, and a muscle layer 420. The one or more layers 405, 410, 415, 420 of skin 400 are merely symbolic and do not represent actual depths or proportions of the skin.

Figure 3B:
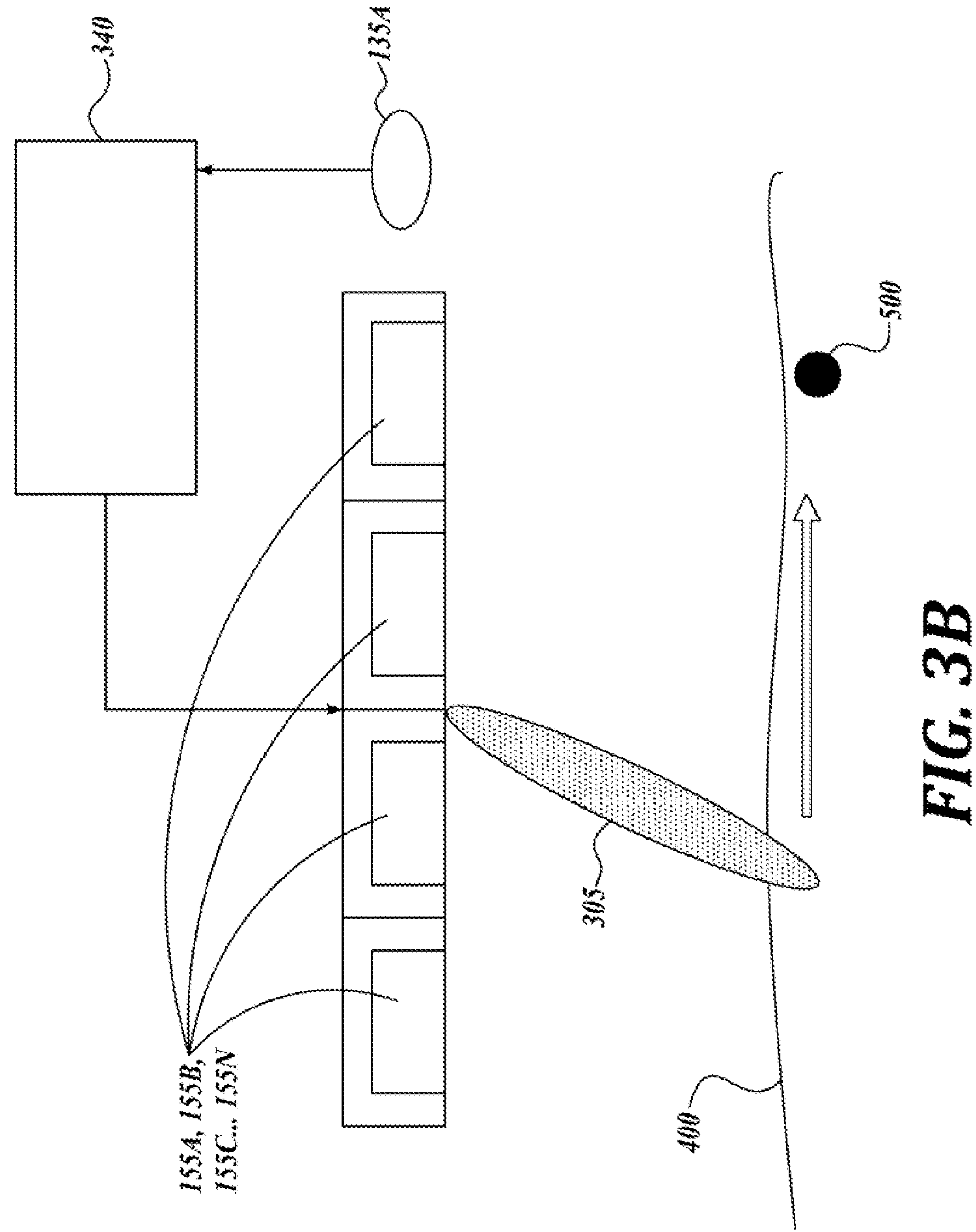
FIG. 3B is another example radiation treatment, in accordance with the present technology.

In some embodiments, the plurality of radiating elements 155A, 155B, 155C . . . 155N are configured to emit one or more beams of radiation 305, 310A, 310B as radiation therapy. While three beams 305, 310A, 310B are illustrated in FIG. 3A, it should be understood that the one or more beams of radiation may be any number of beams, including a single beam, such as shown in FIG. 3B. In some embodiments, the plurality of radiating elements 155A, 155B, 155C . . . 155N are configured to emit a central beam of radiation 305, and one or more lobe beams of radiation 310A, 310B. The central beam of radiation 305 and the one or more lobe beams of radiation 310A, 310B may be collectively referred to herein as "a plurality of radiation beams" and/or "radiation treatment".

In some embodiments, the central beam 305 is configured to extend to a first depth D1 into the skin 400. While the first depth D1 is illustrated as being in the subcutaneous tissue layer 415, it should be understood that the first depth D1 may extend into any layer 405, 410, 415, 420 of the skin 400. In some embodiments, the central beam 305 has a first intensity, a first power level, a first amplitude, and a first frequency. In some embodiments, one or more sensors (such as one or more sensors 135A, 135B) are configured to detect a condition of the skin 400. The one or more sensors may transmit the condition of the skin to a processor (such as applicator processor 140, 240). The processor may then adjust the first intensity, the first power level, the first amplitude, the first frequency, or a combination thereof of the central beam 305.

In some embodiments, the plurality of radiating elements 155A, 155B, 155C . . . 155N are configured to emit one or more lobe beams 310A, 310B. In some embodiments, the one or more lobe beams 310A, 310B are mirrored, that is they extend from each side of the central lobe 305, at substantially the same depth D2. In some embodiments, the one or more lobe beams 310A, 310B each have a second intensity, a second power level, a second amplitude, and/or a second frequency. In some embodiments, the one or more lobes 310A are controlled by a processor in tandem, that is, adjusting the second depth D2, the second intensity, the second power level, the second amplitude, and/or the second frequency of one lobe beam of the one or more lobe beams 310A, 310B, adjusts the second depth D2, the second power level, the second amplitude, and/or the second frequency of all lobe beams of the one or more lobe beams 310A, 310B.

In some embodiments, each lobe beam of the one or more lobe beams 310A, 310B are controlled independently. In such embodiments, each lobe beam of the one or more lobe beams 310A, 310B may extend to a different depth, have a different intensity, a different power level, a different amplitude, and/or a different frequency.

In some embodiments, the first depth D1 is deeper than the second depth D2. In some embodiments, the first depth D1 is equal to the second depth D2. In some embodiments, the first intensity of the central lobe 305 is higher than the second intensity of the one or more lobe beams 310A, 310B. In such embodiments, the radiation treatment 305, 310A, 310B includes applying radiation energy in the form of the central beam 305 at the first intensity at the first depth D1, and radiation energy in the form of the one or more lobe beams 310A, 310B at a second depth D2.

FIG. 3B is another example radiation treatment 305, in accordance with the present technology. In some embodiments, the applicator is configured to administer radiation treatment 305 substantially equally to one or more layers of the skin 400. In some embodiments, the radiation treatment (or central lobe) 305 may be directed towards a condition 500, also referred to herein as one or more treated areas. In some embodiments, the one or more treated areas 500 may be one or more areas where one or more formulas have been applied.

In some embodiments, the applicator and/or system (such as shown in FIGS. 1A-2B and 4-5) includes a plurality of radiating elements 155A, 155B, 155C . . . 155N configured to emit a central beam 305 of radiation energy. In some embodiments, each radiating element of the plurality of radiating elements 155A, 155B, 155C . . . 155N have a common frequency with a common phase shift, in order to emit the central beam 305. The one or more radiating elements 155A, 155B, 155C . . . 155N may also be configured to direct the central beam 305 to one or more conditions 500 on or in the skin 400. In some embodiments, the system includes a processor 340, and a condition sensor 135A. It should be understood that the applicator may also include any of the components illustrated and described in FIGS. 1A-2B, which have been omitted here for clarity. Further, in some embodiments, the radiating elements 155A, 155B, 155C . . . 155N may be a standalone device or separate energy capsule, including one or more radiating elements 155A, 155B, 155C . . . 155N and/or a processor (such as shown in FIG. 3B).

In operation, the condition sensor 135A determines or detects one or more conditions 500 of the skin 400 and the applicator moves across the skin 400. In some embodiments, the one or more conditions 500 include dryness, acne, wounds, fine lines, wrinkles, discoloration, hyperpigmentation, dark circles or spots, liver spots, moles, or the like. While the one or more conditions 500 are illustrated as a single, localized spot, it should be understood that the one or more conditions 500 may include multiple locations or be generalized to an entire portion of the skin, such as in the case of dryness and/or discoloration.

Figure 5:
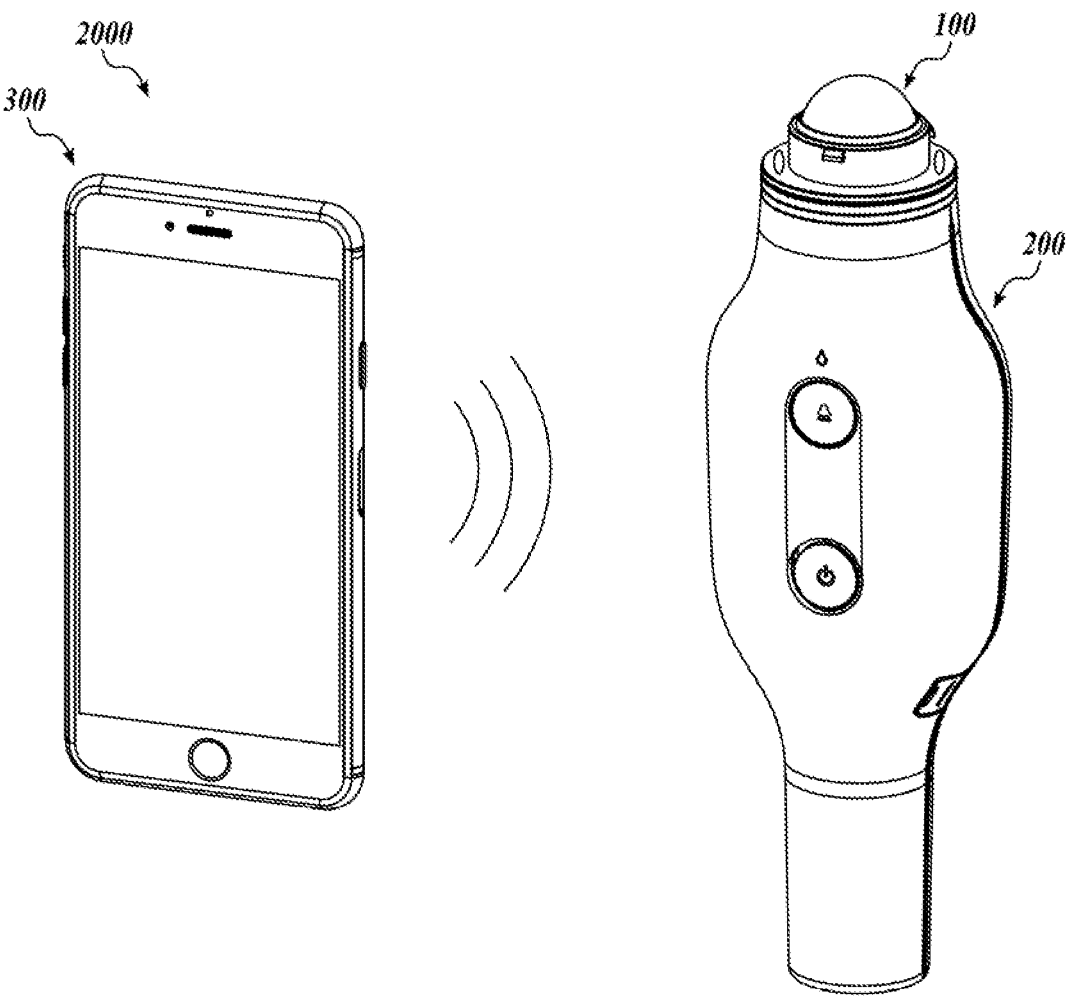
FIG. 5 is another example system, in accordance with the present technology.

After the condition sensor 135 detects or determines the one or more conditions 500 of the skin 400, it transmits the one or more conditions data to the processor 340. In some embodiments, the processor 340 is an applicator processor, such as applicator processor 140, 240. In some embodiments, the processor 340 is a dispenser processor located on or in a dispensing device, such as shown in FIG. 4. In some embodiments, the processor 340 is a smart device processor, located on a smart device, such as shown in FIG. 5. In some embodiments, the processor 340 may be one or more processors, located on the applicator, the dispensing device, and/or the smart device. The processor 340 may receive the one or more conditions data and determine a first depth, a first power level, a first intensity, a first frequency, a first amplitude, or a combination thereof of the central lobe 305. In some embodiments, an identity, a severity, or a location of the one or more conditions informs the first depth, the first power level, the first intensity, the first frequency, the first amplitude, or a combination thereof of the central lobe 305. In some embodiments, the processor 340 directs the plurality of radiating elements 155A, 155B, 155C . . . 155N to direct the central lobe 305 towards the one or more conditions 500. In some embodiments, the processor 340 further directs the plurality of radiating elements 155A, 155B, 155C . . . 155N to emit the central lobe 305 at the first depth, the first power level, the first intensity, the first frequency, the first amplitude, or a combination thereof.

In some embodiments, as the applicator continues to move across the skin 400, the condition sensor 135A continues to determine and/or detect one or more conditions 500 of the skin 400. In such embodiments, the processor 340 may direct the one or more radiating elements 155A, 155B, 155C . . . 155N to adjust the first depth, the first power level, the first intensity, the first frequency, the first amplitude, or a combination thereof based on the one or more conditions detected. In this manner, the one or more radiating elements 155A, 155B, 155C . . . 155N may dynamically adjust the radiation treatment 305.

Figure 3C:
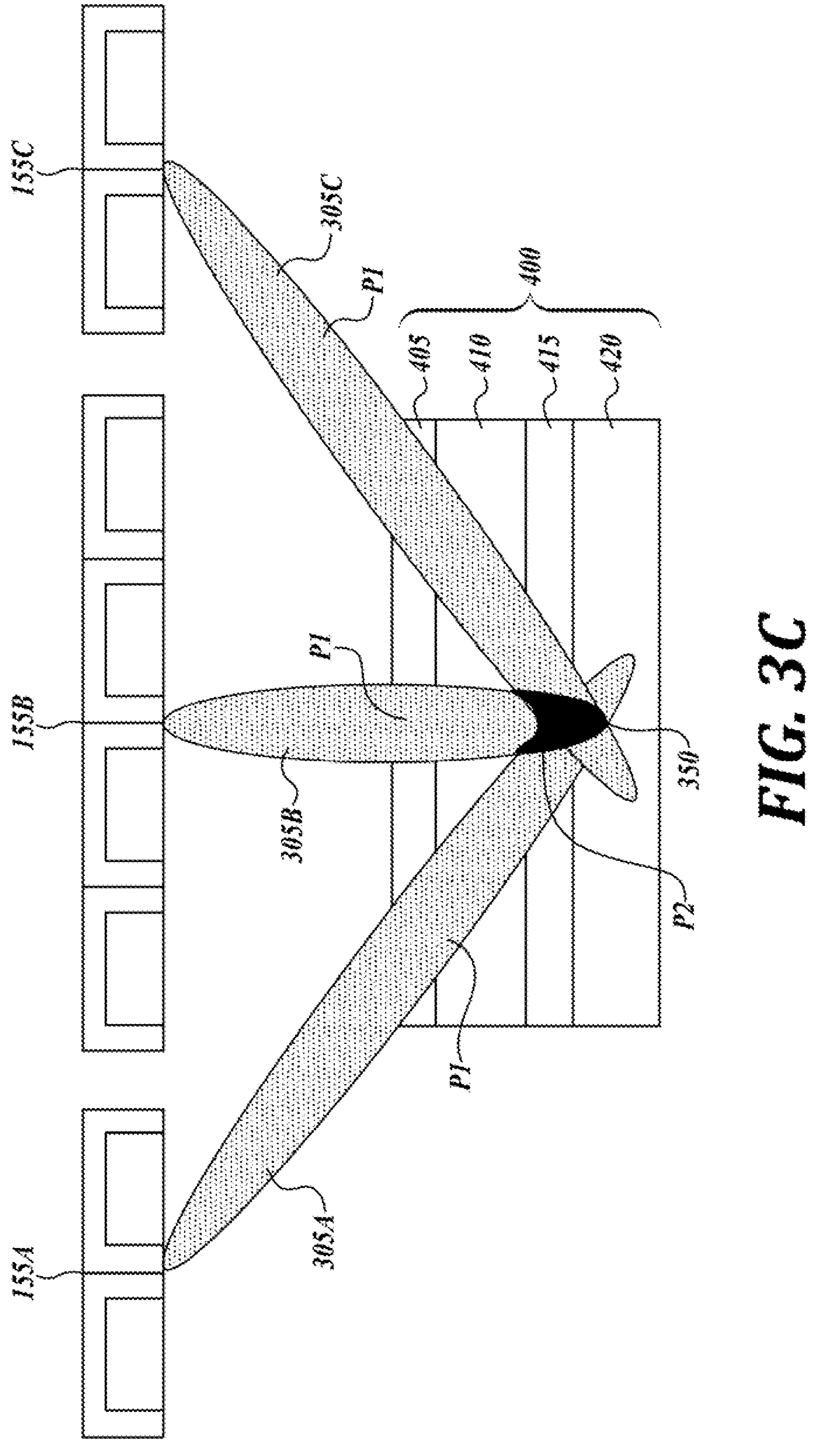
FIG. 3C is another example radiation treatment, in accordance with the present technology.

FIG. 3C is another example radiation treatment 305A, 305B, 305C in accordance with the present technology. In some embodiments, the plurality of are one or more groups of 155A, 155B, 155C. In some embodiments, the one or more groups of radiating elements 155A, 155B, 155C are each configured to emit a beam of radiation 305A, 305B, 305C. In some embodiments, the beams of radiation 305A, 350B, 305C are referred to herein as a plurality of radiation beams 305A, 305B, 305C. In some embodiments, the radiating elements 155A, 155B, 155C may be incorporated into a standalone device or separate energy capsule, not including an applicator. In some embodiments, the radiating elements 155A, 155B, 155C may be a standalone device or separate energy capsule, including one or more radiating elements 155A, 155B, 155C, a processor 340, and one or more sensors 135A.

The one or more groups of radiating elements 155A, 155B, 155C may configured to administer radiation treatment 305A, 350B, 305C into one or more layers 405, 410, 415, 420 of skin 400. The skin 400 includes an epidermis layer 405, a dermis layer 410, a subcutaneous tissue layer 415, and a muscle layer 420. The one or more layers 405, 410, 415, 420 of skin 400 are merely symbolic and do not represent actual depths or proportions of the skin.

In some embodiments, the one or more groups of radiating elements 155A, 155B, 155C are each configured to emit a radiation beam 305A, 305B, 305C, and direct each radiation beam 305A, 305B, 305C to a treatment zone 350. In some embodiments, the treatment zone 350 may be one or more conditions. In some embodiments, each radiation beam 305A, 305B, 305C is emitted at a first intensity P1. In some embodiments, as each radiation beam 305A, 305B, 305C is directed to the treatment zone 350, the plurality of beams 305A, 305B, 305C overlap and focus radiation energy at a second intensity P2 at the treatment zone 350. In some embodiments, the second intensity P2 is higher or stronger than the first intensity P1.

While the treatment zone 350 is illustrated as located in the muscle layer 420, the subcutaneous tissue layer 415, and the dermis layer 410, it should be understood that the treatment zone 350 may be located anywhere within the skin 400. In some embodiments, the treatment zone 350 may be located in a single layer 405, 410, 415, 420 of the skin 400.

In operation, the one or more groups of 155A, 155B, 155C may each emit a beam of radiation 305A, 305B, 305C towards the treatment zone 350 at a first intensity P1. As the plurality of radiation beams 305A, 305B, 305C overlap at the treatment zone 350, the radiation energy focuses at a second intensity P2 in the treatment zone 350. Accordingly, while one or more layers 405, 410, 415, 420 of the skin 400 may receive radiation energy (in the form of the plurality of radiation beams 305A, 305B, 305C) at the first intensity P1, other layers 405, 410, 415, 420 of the skin 400 may receive radiation energy (in the form of the plurality of radiation beams 305A, 305B, 305C) at the second intensity P2. In some embodiments, the second intensity P2 is higher than the first intensity P1.

It should be understood that the radiation treatments illustrated in FIGS. 3A-3C are not mutually exclusive, that is, a single applicator may be configured to emit the radiation treatment of FIG. 3A, the radiation treatment of FIG. 3B, the radiation treatment of FIG. 3C, or combinations thereof either one at a time or simultaneously.

FIG. 4 is an example system 1000, in accordance with the present technology. In some embodiments, the system 1000 includes an applicator 100 and a dispensing device 200. In some embodiments, the applicator 100 can be attached to the dispensing device 200. In some embodiments, the dispensing device includes one or more light sources 220A, 220B, and an actuator 230. In some embodiments, the one or more light sources 220A, 220B may be located on the dispensing device 100, the applicator 100, or both. In some embodiments, either the dispensing device 200 or the applicator 100 includes one or more sensors 135.

In some embodiments, the dispensing device 200 includes an end 210. The end 210 may be configured to be visible through the platform 120 on the applicator 100. In some embodiments, the end 210 includes one or more light sources 220A, 220B configured to administer light treatment to a surface while one or more formulas are being applied, while radiation treatment is being applied, or a combination thereof.

In some embodiments, the one or more light sources 220A, 220B on either the dispensing device 200 or the applicator 100 are LEDs. In some embodiments, there are only two light sources 220A, 220B on the dispensing device. In some embodiments, a first light source 220A is configured to administer light therapy in a first wavelength. In some embodiments, a second light source 220B is configured to administer light therapy in a second wavelength. In some embodiments, the light therapy in the first wavelength and the light therapy in the second wavelength are administered simultaneously. In some embodiments, the light therapy, applying the one or more formulas happens, and/or applying the one or more radiation treatments happens simultaneously.

In some embodiments, the dispensing device 200 includes one or more actuators 230. While the actuators 230 are illustrated as buttons, in some embodiments, the actuators 230 may be switches, capacitive touch type buttons, dials, or the like. The one or more actuator 230 may be configured to begin the administration of light therapy, to apply the formula, or both. In some embodiments, the one or more actuators 230 include a power button 235 and an application button 245. In some embodiments, the power button 235 is configured to turn the dispensing device on or off, while the application button 245 is configured to administer one or more treatments described herein, including light treatment, radiation treatment, or the application of one or more formulas. In some embodiments, the dispensing device 200 further includes one or more sensors 135 configured to detect a condition of the portion of the skin. In some embodiments, the one or more sensors 135 are located on the applicator 100, the dispensing device 200, or a combination thereof. In some embodiments, the dispensing device 200 further includes a dispenser processor 255. In some embodiments, the dispenser processor 255 is configured to direct the applicator 100, the dispensing device 200, or both to administer one or more treatments in response to a condition detected by the one or more sensors 135. In some embodiments, the dispensing device 200 also includes a contact-less chip reader (not pictured in FIG. 4) to read the tag 115 on the applicator 100.

In operation, a user may place an applicator 100 into the dispensing device 200. When the actuator 230 is actuated (such as by pressing the application button 245), the formula is applied, the light therapy is administered, the radiation therapy is administered or some combination is applied, concurrently or simultaneously.

FIG. 5 is another example system 2000, in accordance with the present technology. The system, which implements an applicator 100 and a dispensing device 200 as described herein, further includes and a connected communication device 300. Optionally, the system may further include one or more external servers which are implemented as part of a cloud-computing environment.

The communication device 300 may be a personal computer (PC), a laptop computer, a PDA (Personal Digital Assistants), a smart phone, a tablet device, a UMPC (Ultra Mobile Personal Computer), a netbook, or a notebook type personal computer. In the below examples, the connected device 300 is assumed to be a smartphone, such as an Apple iPhone.

The communication device 300 is capable of performing wireless communication with the dispensing device 300 by way of a wireless communication interface circuitry on the dispensing device 200 or the applicator 100. However, communication device 300 is also capable of having a wired connection to the dispensing device 200 by way of a USB interface. Additionally, the applicator 100 and the dispensing device 200 may communicate with each other and the communication device 300 through an internet connection via an 802.11 wireless connection to a wireless internet access point, or a physical connection to the internet access point, such as through an Ethernet interface. Each connected communication device 300 is capable of performing wireless communication with other devices, such as through a Bluetooth connection or other wireless means as well.

The connected communication device 300 is configured to receive information from a user for use in generating a treatment plan, including one or more treatments, that may be used by the dispensing device 200 to dispense one or more formulas, one or more light treatments, one or more radiation treatments, or a combination thereof.

In some embodiments, the communication device 300 has a related application on it, configured to aid a user in dispensing a formula and/or cleaning an applicator 100. In some embodiments, the application is configured to apply an algorithm to a photo or video of a user to detect one or more conditions. In some embodiments, the conditions may include a dark circle, acne, pigmentation, rosacea, wrinkles, fine lines, or wounds. Additionally, in some embodiments, the application is configured to diagnose one or more skin conditions using an AI algorithm. In some embodiments, the communication device 300 receives the condition detected by the one or more sensors 135A, 135B and confirms or adjusts the detected condition with an AI algorithm. In some embodiments, the communication device 300 communicates the detected condition to a user of the system and proposes one or more treatments to be applied by the applicator 100.

In some embodiments, the communication device 300 may further sense one or more environmental conditions with one or more communication device sensors. In some embodiments, the environmental conditions may include temperature, humidity, UV, pollution, and the like. In some embodiments, the application can gather environmental data from other sources such as weather services. In some embodiments, the application can further recommend a formula, comprised of one or more skin ingredients, to the user based on the detected skin feature and/or environmental conditions.

In some embodiments, the user can set up a user profile on the application of the communication device 300. In some embodiments, setting up the user profile includes answering a user questionnaire. In some embodiments, the user questionnaire gives the user a series of inputs including past skin treatment, past use of the applicator, desired skin quality, or skin concern. In some embodiments, the application can solicit feedback from the user regarding their favorite or most effective formulation to help improve the algorithm.

Figure 6:
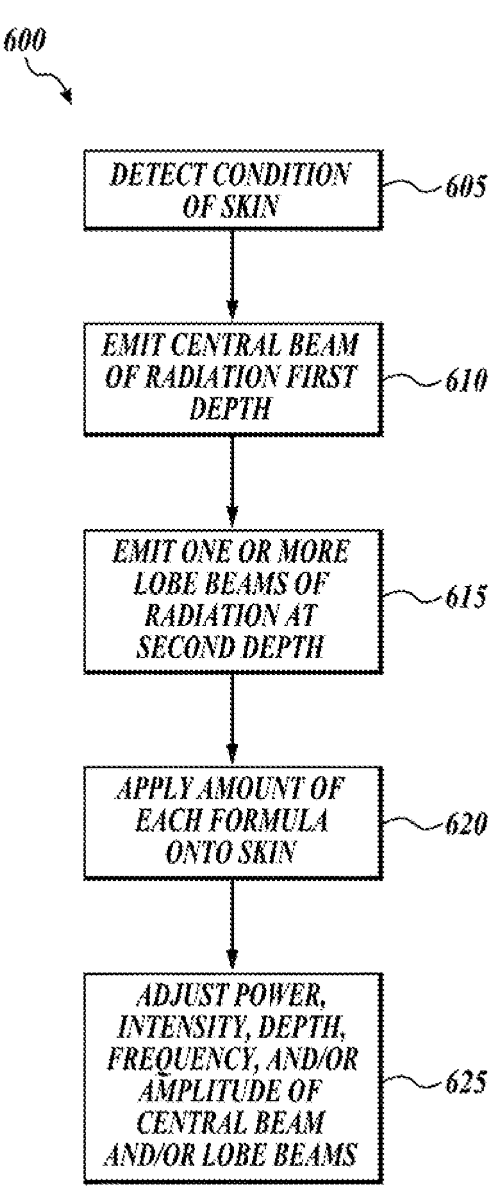
FIG. 6 is an example method of applying a radiation treatment, in accordance with the present technology.

FIG. 6 is an example method 600 of applying a radiation treatment, in accordance with the present technology. In some embodiments, the method 600 is carried out with the applicator or system illustrated in any one of FIGS. 1A-5. Accordingly, in some embodiments, the method is performed by an applicator (such as applicator 100) having an application surface (such as applicator surface 110), one or more sensors (such as one or more sensors 135A, 135B), one or more radiating elements (such as one or more radiating elements 155A, 155B, 155C), and an applicator processor (such as applicator processor 140, 240). In some embodiments, the applicator is inserted into a dispensing device (such as dispensing device 200). In some embodiments, the system includes a smart device (such as smart device 300). An example of the method 600 is illustrated in FIG. 3A.

In block 605, a condition of the skin (such as skin 400) is detected. In some embodiments, the condition is detected by one or more sensors (such as a position sensor and/or a condition sensor). In some embodiments, the condition sensor is a hydration sensor, a reflectance sensor, an optical sensor, or the like. In some embodiments, the sensor determines or detects one or more conditions of the skin and transmits this data to a processor. In some embodiments, the processor is an applicator processor, a dispenser processor, a smart device processor, or a combination thereof, as described herein.

In block 610, the applicator emits a central beam of radiation (such as central beam 305 in FIG. 3A) at a first depth (such as D1) into the skin. In some embodiments, the plurality of radiating elements is configured to emit the central beam. In some embodiments, the first depth is at a epidermis layer (such as epidermis layer 405), a dermis layer (such as dermis layer 410), a subcutaneous layer (such subcutaneous layer 415), a muscle layer (such as muscle layer 415), or a combination thereof. In some embodiments, the detected condition determines the first depth. In some embodiments, the detected condition further determines the power level, intensity, frequency, and/or amplitude of the central beam of radiation. For example, in some embodiments, the power level, intensity, frequency, and/or amplitude of the central beam may be determined because the applicator is located on a cheek, nose, eyelid, forehead, or the like of the user. In some embodiments, the power level, intensity, frequency, and/or amplitude of the central beam is determined by a condition, such as acne, redness, dryness, oiliness, or the like.

In block 615, the applicator emits one or more lobe beams of radiation (such as one or more lobe beams 310A, 310B in FIG. 3A) at a second depth (such as D2) into the skin. In some embodiments, block 615 and block 610 happen simultaneously. In some embodiments, the first depth is deeper than the second depth, but in other embodiments, the first depth and the second depth are substantially equal in depth.

In block 620, an amount of each formula is applied to the skin. In some embodiments, the amount of each formula is determined based on the condition detected or the position of the applicator. For example, in some embodiments, the amount/concentration of a first formula of the one or more formulas is determined because the applicator is located on a cheek, nose, eyelid, forehead, or the like of the user. In some embodiments, the amount/concentration of the first formula is determined by a condition, such as acne, redness, dryness, oiliness, or the like. For example, if the first formula was a moisturizer, the concentration or amount of the first formula may be increased when the skin is determined to be dry. Further, the concentration or amount may be reduced when the skin is determined to be red, indicating irritation. It should be understood that in some embodiments, block 620 may happen in tandem with blocks 610 and 615. In some embodiments, block 620 may occur before block 610 and 615.

In block 625, the power, intensity, depth, frequency and/or amplitude of the central beam and/or the lobe beams are adjusted (referred to collectively as "one or more adjustments"). In some embodiments, the one or more adjustments are determined based on a second condition detected as the applicator moves over the skin. In some embodiments, the one or more adjustments are determined based on the position of the applicator on the skin. The method 600 may then return to block 610. In this manner, the applicator can make continuous adjustments of the one or more adjustments as the applicator moves across the skin, adjusting the radiation treatment in real-time.

Figure 7:
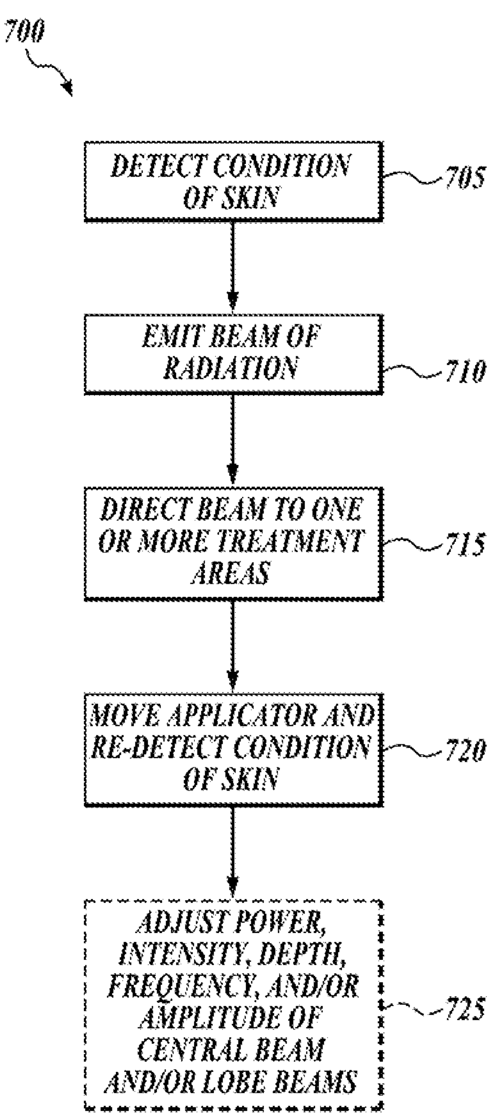
FIG. 7 is another example method of applying a radiation treatment, in accordance with the present technology.

FIG. 7 is another example method 700 of applying a radiation treatment, in accordance with the present technology. In some embodiments, the applicator and/or system discloses herein can perform the method 700. In some embodiments, the applicator and/or system can perform the method 600 and the method 700, either concurrently or separately.

In block 705, a condition of the skin (such as skin 400) is detected. In some embodiments, the condition is detected by one or more sensors (such as a position sensor and/or a condition sensor). In some embodiments, the condition sensor is a hydration sensor, a reflectance sensor, an optical sensor, or the like. In some embodiments, the sensor determines or detects one or more conditions of the skin and transmits this data to a processor. In some embodiments, the processor is an applicator processor, a dispenser processor, a smart device processor, or a combination thereof, as described herein.

In block 710, the applicator emits a central beam (or "beam") of radiation (such as central beam 305 in FIG. 3B). In some embodiments, the plurality of radiating elements is configured to emit the central beam. In some embodiments, the central beam is directed to one or more layers of skin, such as an epidermis layer (such as epidermis layer 405), a dermis layer (such as dermis layer 410), a subcutaneous layer (such subcutaneous layer 415), a muscle layer (such as muscle layer 415), or a combination thereof. In some embodiments, the detected condition determines the depth the beam is emitted.

In block 715, the beam is directed to one or more treatment areas. In some embodiments, the one or more treatment areas are one or more conditions detected with the condition sensor. In some embodiments, the beam is swept across the skin to reach the one or more treatment areas. In some embodiments, the beam delivers radiation energy at a same intensity to multiple layers of the one or more layers of skin. For example, in some embodiments, the beam may deliver radiation energy at a same energy level to an epidermis layer and a dermis layer.

In block 720, the applicator is moved across the skin, and the applicator re-detects another condition of the skin. In some embodiments, as the applicator moves, the condition sensor continuously detects one or more conditions. In this manner, the applicator may monitor the condition of the skin in real time and adjust the application of the one or more formulas or the radiation treatment.

Optionally, in block 725, the applicator adjusts the power, intensity, depth, frequency, and/or amplitude of the beam of radiation in response to the change in condition. For example, if the condition detected is hyperpigmentation, and the hyperpigmentation is centralized in only one area of the skin, the radiation treatment (i.e., beam of radiation) may be adjusted in response to the transition between hyperpigmented skin and non-hyperpigmented skin. In this manner, the applicator may adjust the intensity, depth, frequency, and/or amplitude of the beam of radiation to treat the one or more condition of the skin.

Figure 8:
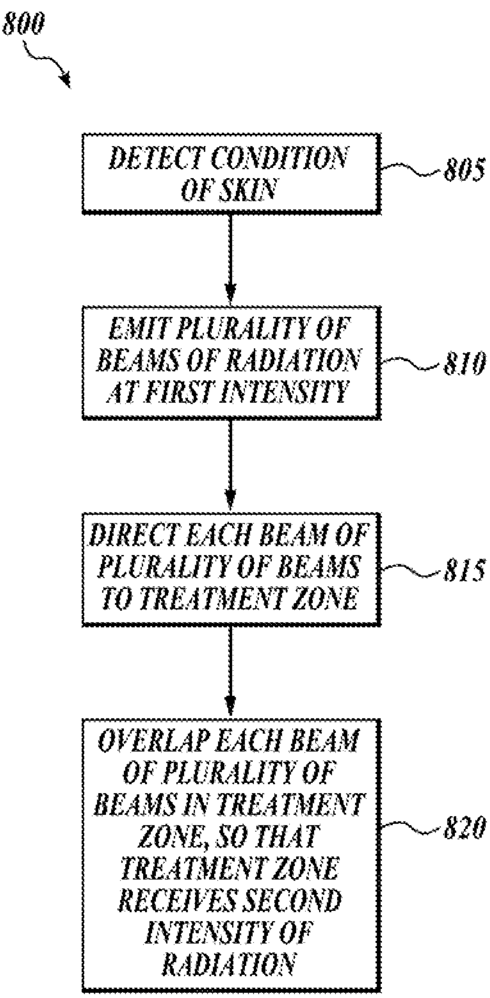
FIG. 8 is another example method of applying a radiation treatment, in accordance with the present technology.

FIG. 8 is another example method 800 of applying a radiation treatment, in accordance with the present technology. In some embodiments, the applicator and/or system discloses herein can perform the method 700. In some embodiments, the applicator and/or system can perform the method 600 and the method 700, either concurrently or separately.

In block 805, a condition of the skin (such as skin 400) is detected. In some embodiments, the condition is detected by one or more sensors (such as a position sensor and/or a condition sensor). In some embodiments, the condition sensor is a hydration sensor, a reflectance sensor, an optical sensor, or the like. In some embodiments, the sensor determines or detects one or more conditions of the skin and transmits this data to a processor. In some embodiments, the processor is an applicator processor, a dispenser processor, a smart device processor, or a combination thereof, as described herein.

In block 810, the applicator emits a plurality of beams of radiation (such as plurality of beams 305A, 305B, 305C in FIG. 3C). In some embodiments, the plurality of radiating elements is configured to emit a plurality of beams. In some embodiments, the plurality of radiating elements are grouped into one or more groups of, and each group of the one or more groups of are configured to emit a beam of the plurality of beams. In some embodiments, the plurality of beams are directed to one or more layers of skin, such as an epidermis layer (such as epidermis layer 405), a dermis layer (such as dermis layer 410), a subcutaneous layer (such subcutaneous layer 415), a muscle layer (such as muscle layer 415), or a combination thereof. In some embodiments, the detected condition determines the depth each beam of the plurality of beams is emitted. Similarly, in some embodiments the intensity depth, frequency, and/or amplitude of the plurality of beams of radiation.

In block 815, each beam of the plurality of beams is directed to a treatment zone. In some embodiments, the treatment zone may be one treatment area of the one or more treatment areas as described herein. In some embodiments, the treatment zone is one or more condition detected with a condition sensor. In some embodiments, the plurality of beams delivers radiation energy at a same intensity to multiple layers of the one or more layers of skin. For example, in some embodiments, the plurality of beams may deliver radiation energy at a same energy level to an epidermis layer and a dermis layer.

In block 820, each beam of the plurality of beams are overlapped in the treatment zone, so that the treatment zone receives a second intensity of radiation energy. In some embodiments, the plurality of beams of radiation are directed to the treatment zone so that the plurality of beams overlap and interact, to deliver a second intensity of radiation energy to the treatment zone. In some embodiments, when each beam of the plurality of beams is emitted at a same intensity, a same frequency, and a same amplitude, overlapping the plurality of beams may be additive, that is, treatment zone will receive a higher second intensity than the one or more layers of skin that are only receiving one beam of the plurality of beams. In another example, if one or more beams of the plurality of beams are emitted at different intensities, different frequencies, and/or different amplitudes, overlapping the plurality of beams may reduce the intensity of the radiation treatment. Accordingly, in some embodiments, the second intensity may be lower than the first intensity.

It should be understood that all methods 600, 700, 800 should be interpreted as merely representative. In some embodiments, process blocks of all methods 600, 700, 800 may be performed simultaneously, sequentially, in a different order, or even omitted, without departing from the scope of this disclosure.

The present application may reference quantities and numbers. Unless specifically stated, such quantities and numbers are not to be considered restrictive, but representative of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the invention.

The embodiments of the invention in which an exclusive property or privilege is claimed are defined as follows:

1. An applicator comprising:

an applicator surface configured to apply one or more formulas;

one or more reservoirs configured to hold the one or more formulas;

one or more sensors, comprising:

a condition sensor configured to determine one or more conditions as the applicator surface moves across skin; and a position sensor configured to determine a position of the applicator on the skin;

one or more radiating elements, wherein the one or more radiating elements are configured to emit one or more radiation treatments into the skin, and wherein the one or more radiation treatments include emitting one or more beams of radiation from the one or more radiating elements;

a tag configured to store and communicate information associated with when to replace the applicator, an amount of the one or more formulas inside the applicator, or an expiration date of the one or more formulas inside the applicator; and a processor configured to:

with the condition sensor, detect the one or more conditions on the skin;

with the condition sensor, determine a location of the one or more conditions based on the position of the applicator; and direct the one or more radiating elements toward the location of the one or more conditions by moving the one or more beams of radiation from a starting location to the location of the one more conditions.

2. The applicator of claim 1, wherein the one or more radiating elements comprise one or more antennas.

3. The applicator of claim 1, wherein the applicator is configured to apply the one or more radiation treatments to one or more areas of formula treated skin.

4. The applicator of claim 1, wherein the processor is further configured to adjust one or more of a power, an intensity, a frequency and an amplitude of the one or more beams of radiation emitted from the one or more radiating elements based on the one or more determined conditions; and wherein the one or more beams of radiation comprise emitting a central beam of radiation, wherein the central beam extends to a first depth.

5. The applicator of claim 4, wherein the one or more beams of radiation further comprise emitting one or more lobe beams, wherein at least one lobe of the one or more lobe beams extends to a second depth;

wherein the one or more lobe beams extend from the central beam; and wherein the processor is further configured to direct the one or more lobe beams independently and adjust one or more of the power, intensity, frequency, and amplitude of the one or more lobe beams independently.

6. The applicator of claim 5, wherein the first depth is deeper than the second depth.

7. The applicator of claim 5, wherein the second depth is deeper than the first depth.

8. The applicator of claim 5, wherein the each of the one or more lobe beams extends to a different depth.

9. The applicator of claim 4, wherein the one or more radiation treatments further comprise emitting the central beam at a first intensity substantially equally to one or more layers of the skin.

10. The applicator of claim 1, wherein the one or more radiation treatments comprise:

emitting a plurality of beams of radiation at a first intensity; and overlapping the plurality of beams of radiation, so that an overlap of the plurality of beams receives radiation energy at a second intensity.

11. The applicator of claim 10, wherein the first intensity is higher than the second intensity.

12. The applicator of claim 10, wherein the first intensity is lower than the second intensity.

13. A system of applying a radiation treatment, the system comprising:

the applicator of claim 1; and a dispensing device configured to couple with the applicator, the dispensing device comprising:

a processor configured to:

direct the dispensing device to apply the one or more radiation treatments; and direct the dispensing device to apply the one or more formulas to the skin.

14. The system of claim 13, wherein the system further comprises a communication device communicatively coupled with the dispensing device.

15. A method of using the system of claim 13, wherein the method comprises:

applying the one or more formulas to the skin; and applying the one or more radiation treatments to the skin.

16. The method of claim 15, wherein the method further comprises:

emitting a central beam of radiation at a first depth.

17. The method of claim 16, wherein the method further comprises:

directing the central beam of radiation and the one or more lobes of radiation to the one or more conditions.

18. The method of claim 15, wherein the method further comprises:

emitting one or more lobes of radiation at a second depth.

19. The method of claim 15, wherein the method further comprises:

emitting a plurality of beams of radiation at a first intensity; and overlapping the plurality of beams of radiation, so that an overlap of the plurality of beams receives radiation energy at a second intensity.

* * * * *